(12) United States Patent
Weisinger

(10) Patent No.: US 7,461,542 B2
(45) Date of Patent: Dec. 9, 2008

(54) FUNNEL VISCOSIMETER

(76) Inventor: Michael S. Weisinger, 291 Mable, Conroe, TX (US) 77301

( * ) Notice: Subject to any disclaimer, the term of this patent is extended or adjusted under 35 U.S.C. 154(b) by 60 days.

(21) Appl. No.: 11/391,118

(22) Filed: Mar. 28, 2006

(65) Prior Publication Data

US 2007/0227234 A1 Oct. 4, 2007

(51) Int. Cl.
*G01N 11/06* (2006.01)
*B65B 39/00* (2006.01)
*B67C 11/04* (2006.01)

(52) U.S. Cl. .............. 73/54.13; 141/331; 141/334; 141/335; 141/336; 222/460

(58) Field of Classification Search ........... 73/54.13; 141/331, 334, 335, 336; 222/460
See application file for complete search history.

(56) References Cited

U.S. PATENT DOCUMENTS

| | | | | |
|---|---|---|---|---|
| 326,566 A | * | 9/1885 | Jochum | 141/298 |
| 343,871 A | * | 6/1886 | Van Kamman | 141/344 |
| 3,074,266 A | * | 1/1963 | Sadler et al. | 73/54.13 |
| 3,748,201 A | * | 7/1973 | Jordan | 149/108.8 |
| 4,184,771 A | * | 1/1980 | Day | 366/3 |
| 6,474,143 B1 | * | 11/2002 | Herod | 73/54.01 |
| 7,114,536 B2 | * | 10/2006 | Guthrie | 141/337 |
| 2006/0209626 A1 | * | 9/2006 | Kojima et al. | 366/173.2 |

FOREIGN PATENT DOCUMENTS

JP 60-52422 A * 3/1985

OTHER PUBLICATIONS

OFI Testing Equipment, INC.—OFITE Plastic Marsh Funnel Viscometer, Mar. 17, 2004, p. 1.*
M.J. Pitt, The Marsh Funnel and Drilling Fluid Viscosity: A New Equation for Field Use, SPE Drill, & Completion, Mar. 2000, pp. 3-6.
Hallan N. Marsh, Properties and Treatment of Rotary Mud, American Institue of Mining & Metallurgical Engineers, Oct. 1930, pp. 234-249.
USPTO web search, Hits 1 thru 41, Refine search "Marsh Funnel".

* cited by examiner

*Primary Examiner*—Daniel S Larkin
(74) *Attorney, Agent, or Firm*—Claude E. Cooke, Jr.; Burleson Cooke L.L.P.

(57) ABSTRACT

A Marsh funnel is equipped with a valve at the funnel outlet. The valve may be of the quick opening type selected from stem valves (internal of the funnel), ball valves, plug valves, flapper valves, butterfly valves, slide valves and the like.

6 Claims, 7 Drawing Sheets

US 7,461,542 B2

FUNNEL VISCOSIMETER

BACKGROUND OF THE INVENTION

This invention relates generally to an improved viscosimeter of the type used in the drilling industry. In one aspect it relates to the method and apparatus for measuring the funnel viscosimeter of a drilling fluid. Another aspect of the invention relates to an improved Marsh funnel.

Consistent with the terminology used in the drilling industry, the terms used herein will have the following meanings:

"viscosity" is broadly defined as a resistance to flow;

"funnel viscosity" is defined as the time (seconds) required for a predetermined volume (one quart or one liter) of mud to flow out of a funnel viscosimeter into a graduated mud cup;

"mud" is defined as a water-based or oil-based drilling fluid containing gelling agents and other additives used in the drilling of oil wells, water wells, gas wells, injection wells, horizontal drilling, and all other areas of the industry.

Viscosity is one of the most important properties of a mud used in the rotary drilling methods. For this reason the mud is tested periodically (usually several times a day) to insure that the viscosity meets the design specification for the drilling fluid. In field operations, a funnel viscosimeter (known as the Marsh funnel) is the industry standard (see API Specification 13-B) and is used extensively throughout the drilling industry. Its use is simple, quick, fool-proof, and thoroughly familiar to field personnel.

The Marsh funnel is a conical-shaped funnel of specific dimensions (defined below) and has become the standard to the extent that the term "Marsh viscosity" or "Marsh funnel viscosity" is synonymous with funnel viscosity.

The funnel viscosity provides an indication of the viscosity (sometimes referred to as "apparent viscosity") but does not provide a measurement of viscosity in conventional units. An article entitled "The Marsh Funnel and Drilling Fluid Viscosity: A New Equation for Field Use" [(SPE Drill & Completion 15, Vol. 15, No. 1 (March 2000)] correlated Marsh funnel measurements with conventional viscosity units. The disclosure of this article is incorporated herein by reference including the references cited therein. Although the Marsh funnel results are purely empirical, it is still widely used throughout the world.

The use of the Marsh funnel, however, presents certain operational problems. The operator responsible for testing the mud generally uses the following procedure: the mud sample is collected by placing the funnel in the drilling mud stream, (usually in the sample box), the mud being retained in the funnel by the operator holding his index finger over the funnel outlet orifice. In measuring the funnel viscosity, the operator releases or removes his finger from the opening while measuring the efflux time of the mud from the funnel. The number of seconds measured for the discharge of a quart (or liter) of mud from the funnel is the funnel viscosity.

This sampling and testing procedure is not as simple or fool-proof as it seems. To begin with, the operator is exposed to drilling mud. For deep wells, the mud is hot and can be painful to the touch. Also, the sampling and testing is cumbersome. Carrying the mud-filled funnel to the testing place requires both hands, one hand being used to carry the funnel and the other hand holding a finger over the orifice. At the testing place, the operator places the funnel in a stand with his finger retained over the orifice and then operates a stop watch with his free hand. Thus, it will be appreciated by those skilled in the drilling industry that this simple procedure not only ties up the operator for several minutes several times a day but presents risks of spillage or leakage from the funnel. This can lead to inaccuracies in the measurements. Also, the operator's movement around a slippery and muddy rig with both hands occupied is clearly an unsafe practice. In summary, there is a need to improve the funnel viscosimeter while retaining the simplicity and the reliability of the procedure.

BRIEF SUMMARY OF THE INVENTION

An object of the present inventor is to provide a modified funnel viscosimeter (e.g. Marsh funnel) that expedites the collection and testing of the mud.

The modified funnel includes a mechanical device for selectively closing the outlet of the funnel. The mechanical device is preferably a quick opening valve operable by a valve actuator (e.g. a trigger). A timer may be linked to the actuator so that opening the valve simultaneously starts the timer. The method of the present invention embodies the simultaneous actuation of the valve and timer.

DETAILED DESCRIPTION OF THE INVENTION

As mentioned above, the present invention, in one aspect, is an improvement of a funnel viscosimeter, represented by the Marsh funnel. The present invention will be described with specific reference to the Marsh funnel, but it is to be emphasized that the principles embodied therein may be used to improve any type of funnel viscosimeter.

Figure 1:
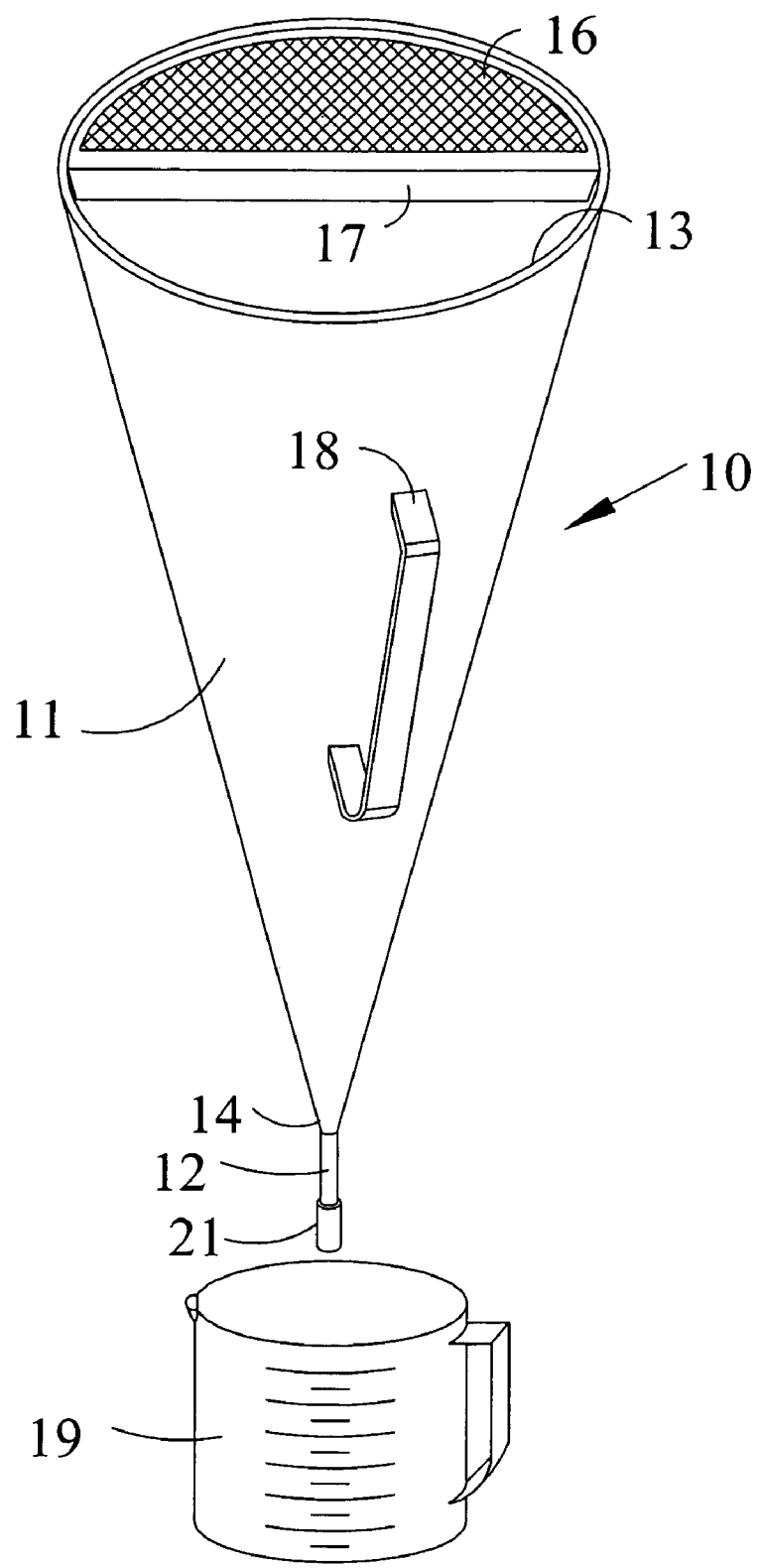
FIG. 1 is a perspective view of a Marsh funnel modified in accordance with one aspect of the present invention.

With reference to FIG. 1, funnel 10 is illustrated as comprising a conical section 11 and a tubular orifice section 12. The funnel has a large opening 13 and tapers to apex 14 which is integral with the tubular orifice section 12. Formed in the tubular section 12 is an orifice passage 20 shown in FIG. 2. The funnel 10 may also be provided with a screen 16 covering a portion of opening 13, a cross-brace 17 for maintaining the screen 16 in place, and a handle 18.

The Marsh funnel as defined in API Specification 13-B has the following approximate dimensions:

a) length of conical section 11 is 12 inches;
b) opening 13 of conical section 11 is 6 inches;
c) length of tubular section 20 is 2 inches;

d) diameter of orifice passage is 3/16 inches;
e) aspect ratio of the conical section 11 is 2:1.

The conventional use of the Marsh funnel in determining the viscosity of a drilling mud as follows: the operator with his index finger over the tip of orifice passage 20 collects the mud through screen 16 from the flowing drilling mud (usually at the sample box) until the mud reaches a level just below the screen 16. The mud is drained from the funnel 10 into graduated cup 19 by the operator removing his finger from the orifice passage 20 while measuring with a stopwatch the time for one quart of the mud to exit the funnel 10. This time is referred to as the funnel viscosity or Marsh funnel viscosity.

In accordance with a broad feature of the present invention, a mechanical device 21 is used to selectively close the orifice passage 20 and thereby obviate the need for the operator to wrestle with the funnel 10 in holding his finger over the orifice passage 20.

Figure 2:
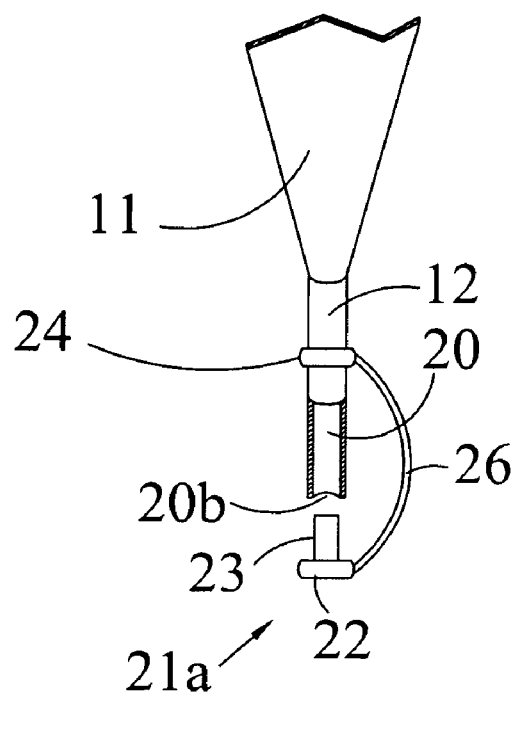
FIG. 2 is an enlarged, partial cross-sectional view of a portion of the funnel shown in FIG. 1 and illustrating a plug for selectively closing the funnel orifice.

One embodiment of the invention is shown in FIG. 2 as comprising a plug 21a. The plug 21a may take many forms but is illustrated in FIG. 2 as comprising a base member 22 and a cylindrical member 23 sized to sealingly and securely fit into the outlet 20b of passage 20. A retainer ring 24 mounted on the tubular section 12 is connected to the plug 21a by strap 26 to ensure that the plug 21a does not become separated from the funnel 10. The cylindrical member 23 of the plug 21a is preferably made of rubber or other elastomeric material.

Figure 3:
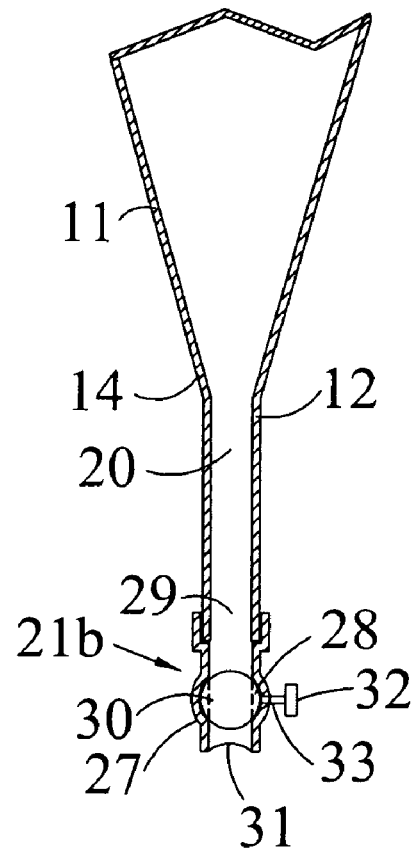
FIG. 3 is a cross-sectional view of a valve attached to a funnel and useable in the present invention.

In a preferred embodiment of the present invention, the mechanical device 21 is a valve shown as 21b in FIG. 3. The valve 21b is a ball valve but, as will be explained below, other types of valves may be also used. All that is required is that the valve be quick opening and have a flow path that does not obstruct the flow of mud from the funnel 10.

The ball valve 21b illustrated in FIG. 3 comprises a housing 27, an internal ball member 28 mounted in the housing 27 and having a ball opening 30 extending therethrough. In the open position of the ball member 28, flow path 30 registers with valve inlet 29 and valve outlet 31. A stem 33, extending through the housing 27 and secured to ball 28 provides means for actuating the valve 21b from the open to the closed position. The stem 33 may be connected to a handle 32 or as described below, may be linked to a remote valve actuator. In the closed position, the path 30 is transverse the direction of the valve inlet and outlet 29 and 31. Ball valves of the type useable in the present invention are commercially available and are well known to those skilled in the art. Accordingly, the valve 21b has been only generally described. The valve 21b may be made of plastic material and attached to the tubular member 12 by plastic cement or glue.

Other valves useable in the present invention characterized as quick opening include butterfly valves, slide valves, flapper valves, hinge valves, plug valves and the like. These valves are commercially available for low pressure service and are readily adapted for use in the present invention.

Figure 4:
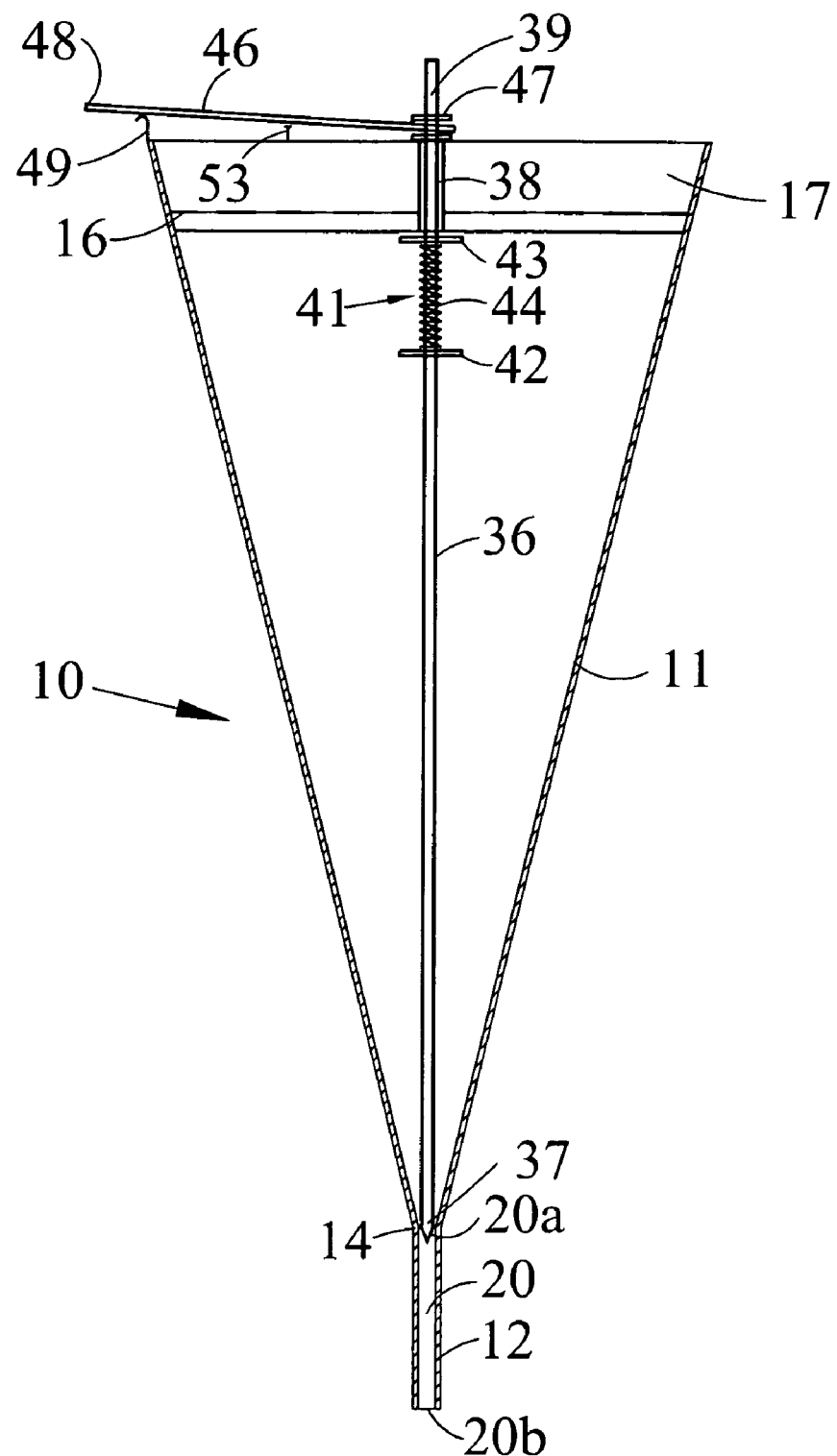
FIG. 4 is a schematic of a Marsh funnel shown in cross section and illustrating an internal valve useable in the present invention.

FIG. 4 illustrates another embodiment and in particular an internal valve assembly for closing inlet 20a of the orifice passage 20. The valve assembly comprises a valve stem 36 extending from the apex 14 of the funnel 10 upwardly through its center and exiting through opening 38 formed in brace member 17. Lower end 37 of the stem 36 is configured and sized to close orifice inlet 20a. The upper end 39 of the stem 36 extends a short distance above brace member 17. A spring assembly 41 maintains end 37 in sealing engagement with inlet 20a of passage 20. The spring assembly 41 comprises opposed washers 42 and 43 urged apart by spring 44, all concentrically mounted on stem 36. The lower washer 42 is secured to stem 36 and the upper washer 43 is sized to permit the movement of stem 36 therethrough. With assembly 41 installed, one end of the spring 44 anchors washer 43 into engagement with the underside of brace member 17 forcing the lower washer 42 and stem 36 downwardly, seating the end 37 into the inlet 20a of orifice passage 20.

The stem end 37 may be moved to the open position by lever 46 acting on stem 36. A spool member 47, (e.g. opposed washers) is secured to upper end 39 of stem 36. Lever 46 has its inner end mounted on spool 47 and its outer end 48 extending a short distance beyond the opening 13 of funnel 10. End 48 of lever 46 is mounted on spool 47 to permit angular movement but not axial movement with respect to stem 36. A bar or projection 53 mounted on brace member 17 serves as a fulcrum for lever 46. The outer end 48 of lever 46 is adapted to be moved and retained in a hook 49 mounted on the tunnel 10 at the periphery of opening 13.

In the normally closed position of the valve, tip 37 engages and closes the inlet 20a of orifice passage 20 by the action of the spring assembly 41 forcing the stem 36 downward. Note that the spool 47 is positioned on the stem 36 to permit the seating of tip 37 in the orifice opening 20a. In this position, the lever 46 has no effect on the stem 36 or spring assembly 41.

Figure 5:
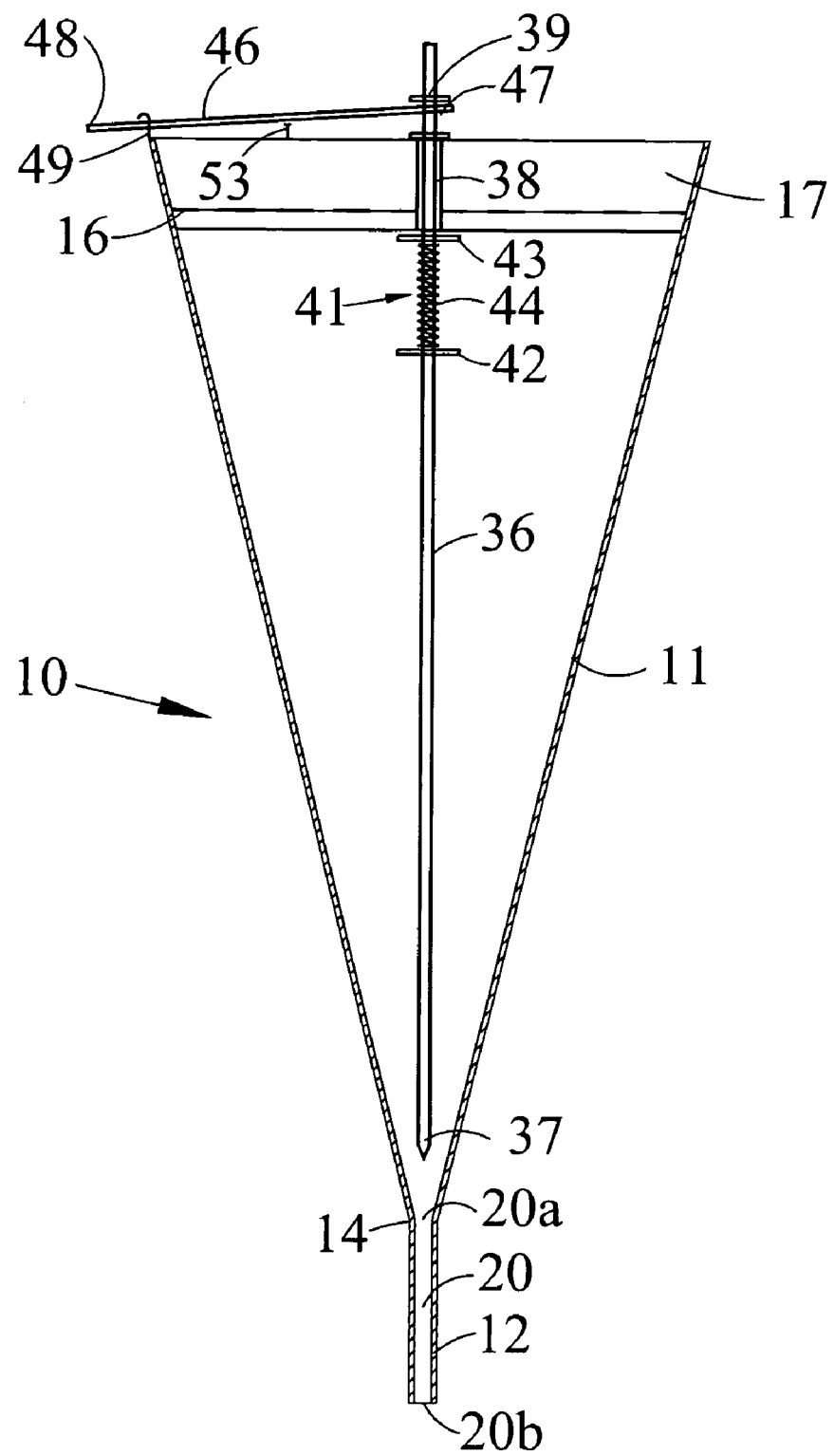
FIG. 5 is a view similar to FIG. 4 showing the internal valve in the open position.

To open the orifice passage 20, the lever 46 is positioned on bar 53 and forced downwardly to move the spool 47 and stem 36 upwardly against the action of spring 44. The lever 46 is anchored by hooking end 48 onto inlet hook 49. The projection 53 is sized to achieve the desired displacement of tip 37 above the inlet 20a. FIG. 5 illustrates the open position of the valve and actuator assembly.

Figures 6, 7:
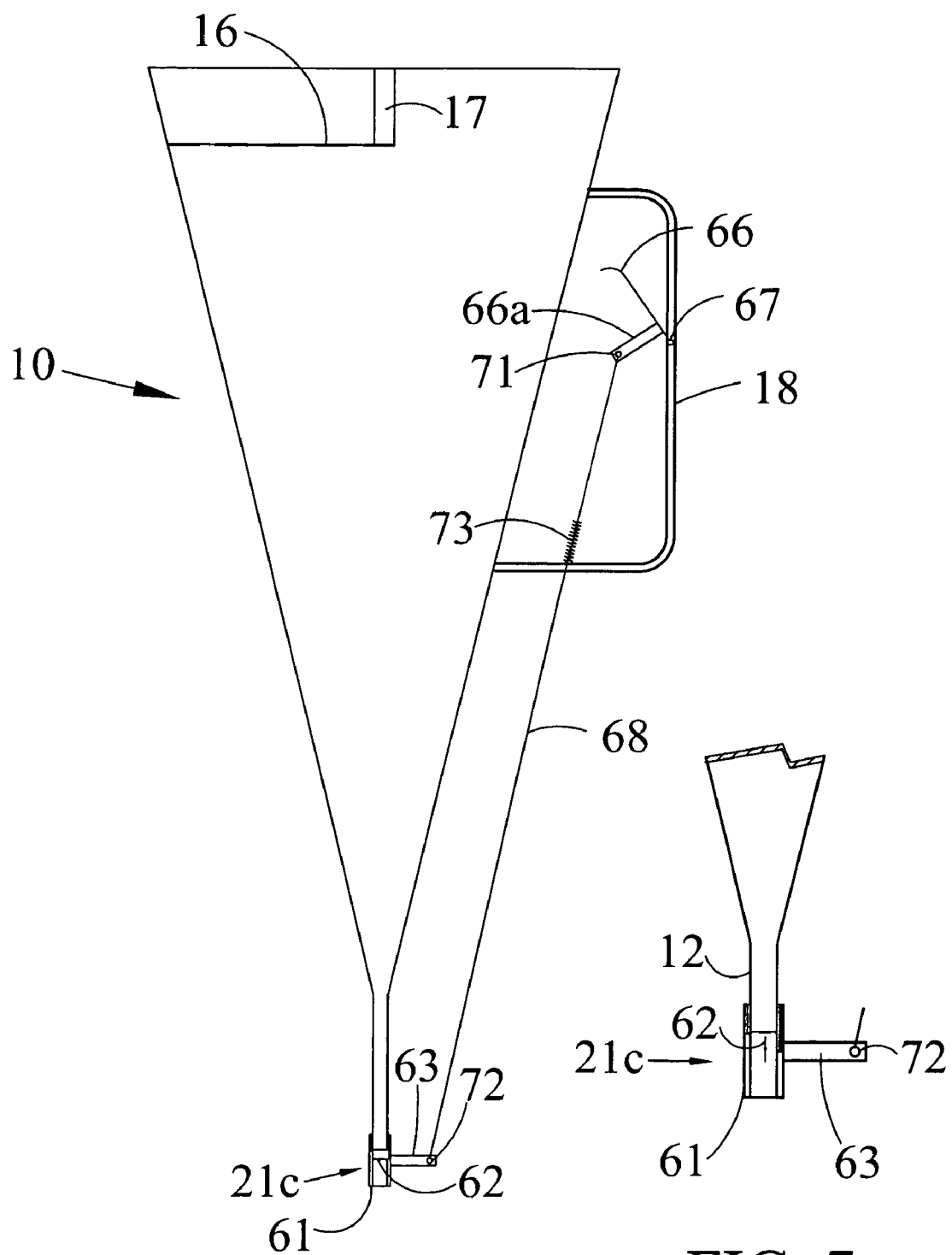
FIG. 6 is a schematic of the Marsh funnel illustrating a valve and a valve actuator useable in the funnel invention.
FIG. 7 is an enlarged cross-sectional view of the valve disclosed in FIG. 6.

Returning to the external valve embodiment of FIG. 3. the valve 21b may be manipulated manually as described above. Preferably, however, a valve actuator is provided on or near the handle 18 of the funnel 10. This feature is illustrated in FIG. 6 where an actuator opens and closes a butterfly valve illustrated as 21c. In this embodiment, the butterfly valve 21c comprises a housing 61 mounted on tube 12, a disk 62 pivotally mounted in the housing 61 and lever 63 for moving the disk 62 between an open and closed positions (see FIG. 7). Butterfly valves are well know to those skilled in the art and need not be described in detail herein. The valve actuator in this FIG. 6 embodiment includes a trigger 66 pivotally mounted on handle 18 as at 67, and a linkage 68 interconnecting trigger 66 and valve lever 63. The linkage 68 interconnects the trigger and the lever 63 at pivot points 71 and 72. Note, the trigger 66 may include a tab or projection 66a for connection to the linkage 68. A tension spring 73 may be employed to maintain the valve 21c in the closed position by biasing the linkage 68 downwardly as viewed in FIG. 6.

Operation of the funnel showing in FIG. 6 is as follows: with the butterfly valve 21c in the closed position, a mud sample is collected in funnel 10 and carried to the testing place. The operator begins the test by pulling trigger 66 while at the same time starting the stopwatch. The trigger 66 opens the butterfly valve 21c and the efflux time of one quart of mud is the funnel viscosity.

Figure 8:
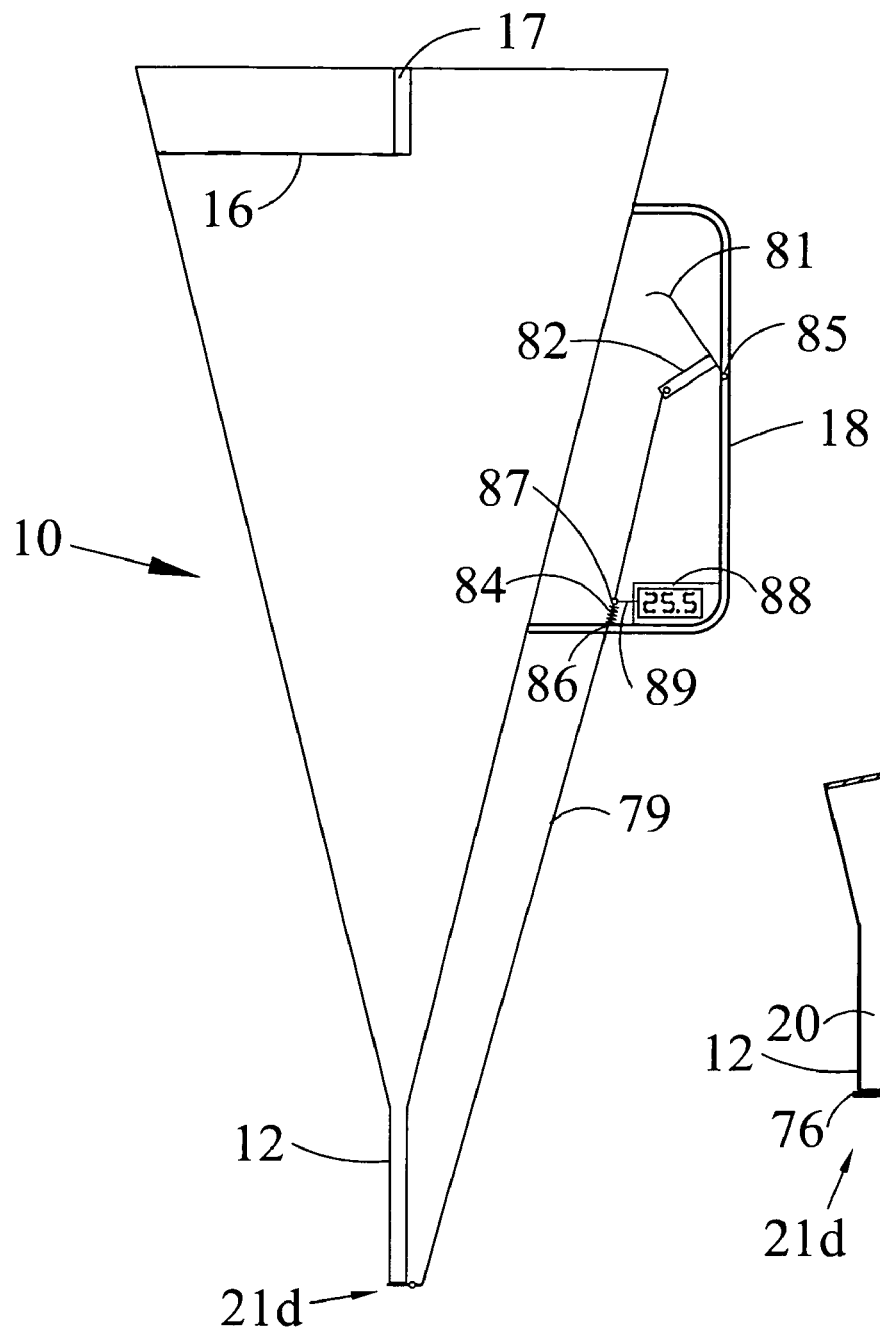
FIG. 8 is a schematic view similar to FIG. 6 and further disclosing a valve actuator linked to a timer.

The embodiment of FIG. 8 is similar to the embodiment of FIG. 6, except a timer for measuring the efflux time, is linked to opening the valve 21c. In this embodiment, however, the valve is illustrated as a flapper valve 21d (also referred to as a hinge valve) comprising a disk 76 pivotally mounted on the tubular section 12 by pivot 77. A lever 78 extends outwardly from the pivot 77 and is secured to a rod 79 at pivot point 78 (see FIG. 9). The upper end of rod 79 is secured to trigger 81 through tab 82 and is pivotally mounted on handle 18 as at pivot point 85.

A spring 84 has one end connected to handle 18 as at 86 and its other end to the rod 79 as at 87. The tension spring 84 thus maintains the valve 21*d* in the closed position to close the orifice passage 20. A timer 88 mounted on handle 18 has an outwardly extending lever 89 secured to rod 79. In the normal position of the trigger 81 and valve 21*d*, the timer 88 is in the off position, but when the trigger 81 is pulled the lever 89 activates the timer 88 to the on position. When the trigger 81 is released, the timer 88 is returned to the off position, displaying the elapsed time. In lieu of tension spring 84, a hinge spring at pivot point 77 may be employed.

Figure 9:
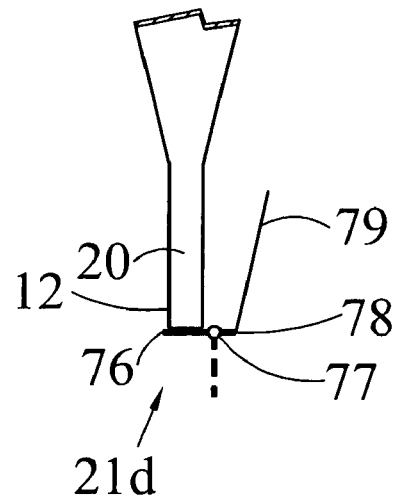
FIG. 9 is an enlarged fragmentary view of FIG. 8 shown in side elevation, illustrating details of a flapper valve.

The operation of the funnel shown in FIGS. 8 and 9 is as follows: the mud is collected in the funnel 10 with the valve 21*d* in the closed position and carried to the place of testing. At the test site, the trigger 81 is pulled, starting the test. The flapper valve 21*d* opens (dotted-line position FIG. 9) while at the same time the timer 88 is turned on. When one quart has drained from the funnel 10, the trigger 81 is released returning the valve 21*d* to the closed position and shutting off the timer 88. The elapsed time is the funnel viscosity of the mud tested. A reset button may be provided on the timer 88 to reset the timer for the next test.

Figure 10:
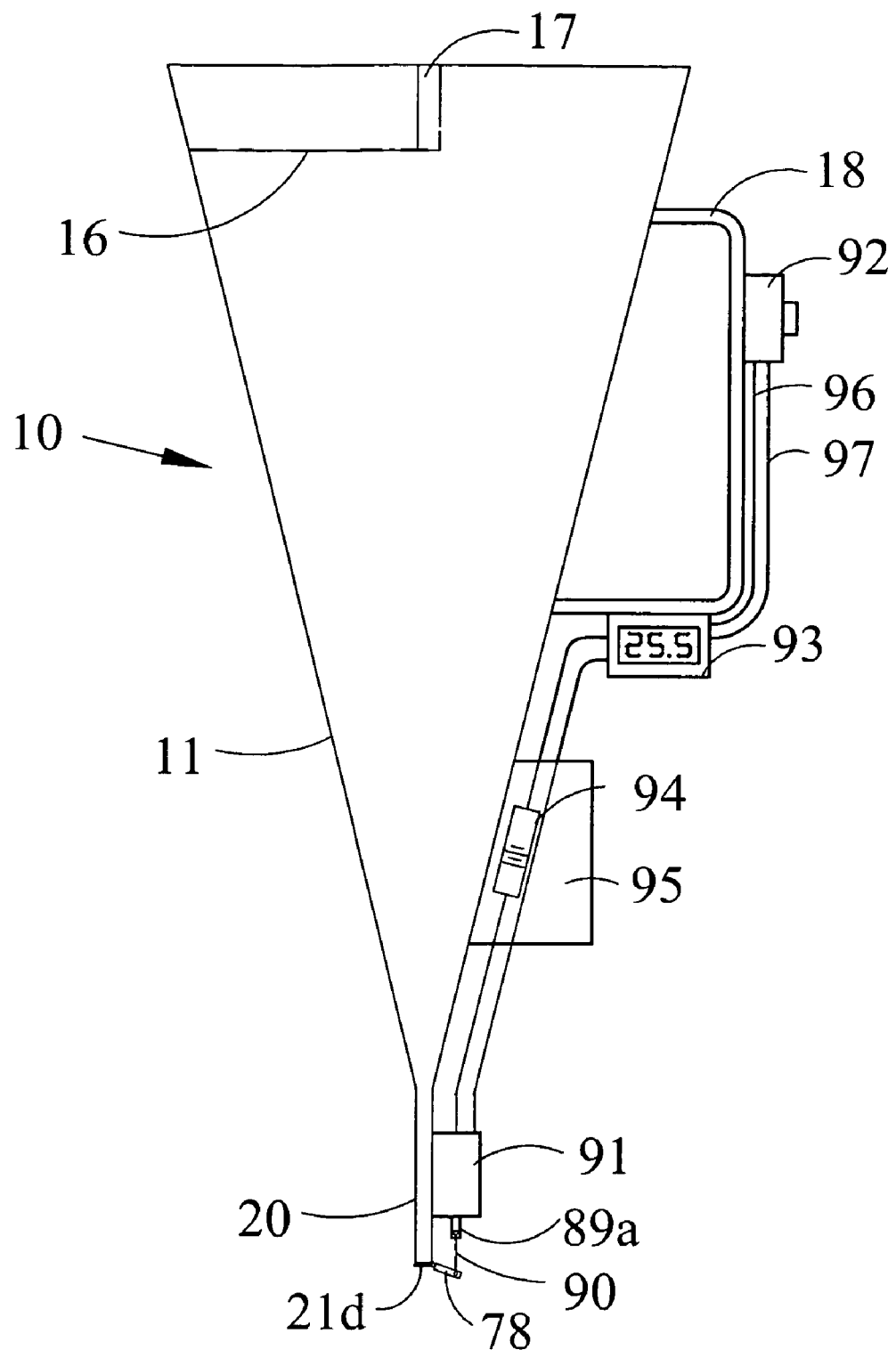
FIG. 10 is a schematic view of a Marsh funnel equipped with a solenoid valve and a switch for electrically activating the solenoid.

The embodiment shown in FIG. 10 is a further refinement of the concept of linking the actuation of the valve 21*d* and the timer 88, except in this embodiment, the linkage is by an electric linkage instead of a mechanical one. As shown in FIG. 10, the flapper valve 21*d* has its lever 78 connected to a solenoid 91. The solenoid 91 is connected in circuit with a starter switch 92, a digital timer 93 and a battery 94 (in housing 95). Conductors 96 and 97 are wired to complete the circuit comprising components 91, 92, 93 and 94. Thus, actuation of switch 92 sends a DC current through timer 93 and solenoid 91. This opens the valve 21*d* by a solenoid plunger 89*a* pulling up on linkage 90 and lever 78.

The operation of the FIG. 10 embodiment is as follows: mud is collected into the funnel 10 and is carried to the place of testing. The funnel 10 may be mounted on a stand with the funnel outlet directed into a graduated cup. The switch 92 is activated sending an electric DC current to the solenoid 91 which opens the normally closed valve 21*d*. At the same time the current activates timer 93 for measuring of the efflux time. When one quart has drained from the funnel 10, switch 92 is again pushed, opening the circuit, stopping timer 93, and closing valve 21*d*. Note that the valve 21*d* is normally closed; it is opened only upon activation of solenoid 91.

EXAMPLE

A Marsh funnel was retrofitted with the valve assembly shown in FIG. 4. The valve stem 36 had a diameter of ¼" and the stem tip 37 was tapered. In the valve's open position, the tip 37 was spaced 5/16" above inlet 20*a*.

The funnel viscosity of tap water was measured to be approximately 25 seconds. The funnel viscosity of water using a Marsh funnel without the valve assembly was also about 25 seconds. Similar tests were also carried using a drilling mud of 9.4 ppg The funnel viscosity of the mud in the standard Marsh funnel and in a modified Marsh funnel in accordance with FIG. 4 were substantially identical [[:]]. approximately 35 seconds.

Again, it is emphasized that the external valves of FIGS. 3, 5 and 7 are interchangeable. These valves, as well as other quick opening valves, include an internal rotary closure member which is movable to an open position, usually by about a 90° turn.

Although the present disclosure has been described in detail, it should be understood that various changes, substitutions and alterations can be made thereto without departing from the scope and spirit of the invention as defined by the appended claims.

What is claimed is:

1. A viscosimeter for measuring the funnel viscosity of a liquid comprising:
   a) a funnel section having an open upper end and a lower apex;
   b) a tubular section connected to the funnel section at the apex and defining an orifice passage, for draining the funnel section, whereby the liquid flows from the funnel section through the orifice passage; and
   c) a mechanical device for selectively closing and opening the orifice passage wherein the mechanical device is a valve mounted on the viscosimeter and being movable between a closed position and an open position to selectively close and open the orifice passage, wherein the valve is mounted internally of the funnel section and comprises a stem extending upwardly within the funnel section having an upper end and a lower end sized to close the inlet of the orifice passage, wherein the stem extends axially through the funnel section and includes a spring for urging the lower end of the stem into engagement with the inlet of the orifice passage, and further includes a valve actuator operative on the upper end of the stem to move the stem upwardly against the spring thereby moving the lower end of the stem away from the inlet of the orifice passage.

2. A viscosimeter for measuring the funnel viscosity of a liquid comprising:
   a) a funnel section having an open upper end amd a lower apex;
   b) a tubular section connected to the funnel section at the apex and defining an
   orifice passage, for draining the funnel section, whereby the liquid flows from the funnel section through the orifice passage; and
   c) a mechanical device for selectively closing and opening the orifice passage wherein the mechanical device is a quick opening, normally closed valve mounted on the viscosimeter on the tubular section and being movable between a closed position and an open position to selectively close and open the orifice passage, and further includes a solenoid adapted to open and close the valve and an electric circuit to the solenoid including a switch for activating the solenoid thereby opening the valve.

3. The viscosimeter of claim 2, further comprising an electric timer in the electric circuit for activating the valve whereby the timer starts upon actuation and stops on deactivation.

4. A viscosimeter for measuring the funnel viscosity of a liquid comprising:
   a) a funnel section having an open upper end and a lower apex;
   b) a tubular section connected to the funnel section at the apex and defining an orifice passage, for draining the funnel section, whereby the liquid flows from the funnel section through the orifice section; and
   c) a mechanical device for selectively closing and opening the orifice passage wherein the mechanical device is a quick opening, normally closed valve mounted on the viscosimeter on the tubular section and being movable between a closed position and an open position to selectively close and open the orifice passage, wherein the valve is mounted on the tubular section to selectively open and close the outlet of the orifice passage, and the viscosimeter further includes a valve actuator for opening the valve, wherein the valve actuator comprises a handle mounted on the funnel section, a trigger pivotally mounted on the handle, and a linkage interconnecting the valve and the trigger, whereby actuation of the trigger opens the valve, and wherein the linkage is mechanical having an upper end connected to the trigger lever and a lower end connected to the valve, and further comprising a timer adapted to be started and stopped by actuation of the mechanical linkage.

5. A funnel viscosimeter comprising:
a) an inverted conical section terminating in a lower apex and having an external handle;
b) a tubular section connected to the apex and defining an orifice passage therethrough whereby liquid flows out of the conical section through the orifice passage;
c) a quick opening valve mounted on the tubular section in registry with the orifice passage and being movable between an open position and a closed position to open and close the orifice passage; and
d) a valve actuator for selectively moving the internal member between an open and closed position wherein the valve actuator includes a switch, a solenoid connected to the rotary member for maintaining the rotary member in the normally closed position, and an electric circuit interconnecting the switch and the solenoid, whereby actuating the switch activates the solenoid and moves the rotary member to the open position.

6. The funnel viscosimeter of claim 5, further comprising a timer mounted in the electric circuit whereby current in the circuit starts the timer and interruption of current stops the timer.

* * * * *